United States Patent [19]

Kobayashi et al.

[11] Patent Number: 5,407,443
[45] Date of Patent: Apr. 18, 1995

[54] LASER OPERATION DEVICE

[75] Inventors: Katuhiko Kobayashi; Takashi Takahashi, both of Tokyo, Japan

[73] Assignee: Kabushiki Kaisha Topcon, Tokyo, Japan

[21] Appl. No.: 163,032

[22] Filed: Dec. 6, 1993

[30]   Foreign Application Priority Data

Dec. 6, 1992 [JP] Japan ................................. 4-351304

[51] Int. Cl.$^6$ ............................................. A61B 17/36
[52] U.S. Cl. ........................................ 606/3; 606/10; 606/16; 385/80
[58] Field of Search ................... 606/10, 11, 12, 15, 606/16, 17, 3; 385/14, 27, 28, 50, 54, 55, 56, 58, 80

[56]   References Cited

U.S. PATENT DOCUMENTS

| | | | |
|---|---|---|---|
| 4,686,979 | 8/1987 | Gruen et al. | 606/15 |
| 4,785,805 | 11/1988 | Joffe et al. | 606/16 |
| 5,078,711 | 1/1992 | Kakami et al. | 606/16 |
| 5,139,494 | 8/1992 | Freiberg | 606/15 |

*Primary Examiner*—Stephen C. Pellegrino
*Assistant Examiner*—Sonya C. Harris
*Attorney, Agent, or Firm*—Brumbaugh, Graves, Donohue & Raymond

[57]   ABSTRACT

A laser operation device for insertion into a region to be irradiated and which is optimally used as an introcular device to treat cataracts, glaucoma or the like. The device has a hand piece and a probe which is to be inserted into the region to be irradiated. A first fiber portion guides light from a laser light source to the hand piece, a second fiber portion connected with the first fiber portion at a connection surface thereof introduces light from the first fiber portion to the region to be irradiated. A first terminal formed to an end of the first fiber portion and a second terminal formed to an end of the second fiber portion are connected by a split sleeve, so that alignment between the first fiber portion and the second fiber portion is facilitated. Buffers around the first fiber and the second fiber protect the respective fibers from damage. Even if the second fiber portion were destroyed, safe and accurate incising operation can be applied to eye tissue or the like.

5 Claims, 5 Drawing Sheets

LASER OPERATION DEVICE

BACKGROUND OF THE INVENTION

The present invention concerns a laser operation device having a hand piece provided with a probe to be inserted into an irradiated region and, more particularly, it relates to a laser operation device which is most suitable as an intraocular operation device for cataract, glaucoma or the like, and in which a fiber portion is not in contact with intraocular tissue even when a top end that emits a laser beam is destroyed by laser energy or the like and, further, a connection portion of the fiber is less damaged by the laser energy.

For a patient suffering from lens opacity caused by cataract, no effective therapeutical agent is known at present for making the lens transparent, so that an operation for extirpation of a clouded lens is necessary for the recovery of impaired vision.

As an operation method for cataract, an ultrasonic emulsifying and sucking method has generally been put to practical use in recent years. Although there has been a limit on the ultrasonic emulsifying and sucking method in that this is effective only to a soft lenticula, a lenticula dividing method has been proposed and the ultrasonic emulsifying and sucking method has now been applied also to a hardened lenticula.

That is, in the lenticula dividing method, a predetermined amount of perfusate is injected between each laminar layer of the lenticula to separate layers from each other thereby softening the lenticula. In the ultrasonic emulsifying and sucking method, an ultrasonic wave at about 27 to 55 KHz is applied to cause vibrations under injection of the perfusate, which induces cavitation and destroys a lens tissue suffering from cataract by the mechanical destroying action thereof, and then emulsified lenticula tissue and the perfusate are sucked.

For a relatively soft lenticula, a lens capsule is at first incised and then a cataract lens tissue is destroyed and sucked by an ultrasonic emulsifying and sucking method. Then, an operation for inserting an artificial lens into the remaining lens capsule is conducted. For incising the lens capsule, a circular incising method is generally used, because the method provides a symmetrical opening, causes less cracking to the periphery of the lens capsule and results in less troubles to eye tissues. Further, since the inserted artificial lens can be kept stably, that possibility of vision impairment caused by axial displacement of the artificial lens after the operation is reduced.

For a lenticula hardened considerably upon further progress of cataract, neither incision of the lens capsule nor the ultrasonic emulsifying and sucking method is applicable but a whole extirpation of removing all the lens capsule is conducted. However, since the intracapsular extirpation leaves no lens capsule, the artificial lens can not be stably fixed in the eye. Accordingly, hydrodelineation is applied by oscillating a top end of a fine wire by ultrasonic waves, injecting perfusion of a balanced salt solution from the top end to defoliate the layers of the lens capsule from each other.

A hand piece using a laser beam has been developed for removing lens tissue in an eye suffering from cataract. The hand piece comprises a hand piece main body, means for transmitting a laser beam at a wave length corresponding to an absorption peak of water, a perfusing means for perfusing a perfusate and a sucking means for sucking tissue evaporated by the laser beam.

The hand piece is provided with a probe for a laser scalpel and the probe uses, for example, ZnSe crystals as a support member for the fiber for protecting an emitting end face of the fiber.

Further, there is a fiber having an outer diameter equal to or greater than that of a laser beam power transmission fiber and attached to the top end of the probe for protecting the end face of the power transmission fiber and focusing or diverging the emitted laser beam.

However, the probe used in the conventional hand piece as described above is inefficient because the shape of a protecting member for the top end of the fiber attached to the top end of the probe is complicated. The protection member for the top end of the fiber has to be fabricated at a high accuracy in order to improve the sealing effect at the top end of the fiber, making it difficult to reduce the diameter of the probe.

When conducting an accurate intraocular operation using the laser probe, it is necessary to reduce the beam diameter of the irradiating laser beam by minimizing the core diameter at the top end. However, since the laser beam irradiated from the top end of the optical fiber diverges from the entire surface of the core at an angle defined by the number of aperture of the fiber, even if the top end of the fiber is fabricated into a convex lens shape or a convex lens is disposed to the top end, it is difficult to focus the irradiating laser beam to smaller than the core diameter of the fiber.

Further, since the support member for the fiber is constituted, for example, with crystals of ZnSe or the like, it can not be said non-toxic to a human body and it is not suitable as a fiber end probe to be inserted into the human body.

Further, for the hand piece using a laser beam, an infrared laser beam at a wavelength of about 2.9 $\mu$m can be used but, since the infrared laser at a wavelength of about 2.9 $\mu$m coincides with a sharp absorption spectrum of —OH group, it involves a problem that transmission, for example, through quartz fiber containing —OH groups in the ingredient is impossible.

Then, as a fiber capable of transmitting a sufficient energy of 2 J/cm$^2$ (energy on the acting surface in an infrared laser beam at a wavelength of about 2.9 $\mu$m) to act on a living body as a laser scalpel, a fiber mainly composed of zirconium type fluoride glass is considered most optimum at present. However, since the zirconium type fluoride glass fiber dissolves, although little, into water to form a fluoride, it involves a problem that it can not be inserted with no coverage into a human body.

Further, for introducing an infrared laser beam at a wavelength of about 2.9 $\mu$m to an irradiation region, when a zirconium type fluoride glass fiber is used for a portion of the fiber, there may be a worry that the connection portion between the fiber and the top end is destroyed by the heat energy of the laser beam at the top end, as well as the possibility that the fiber portion, if it should be destroyed, is in contact with a living body tissue, so that it can not always be considered harmless to the human body.

Dehydrated epoxy type adhesives used for a laser scalpel or the like have properties wherein the molecular weight of the epoxy as a main agent is from 200,000 to 300,000, the molecular weight of the amine as a hardening agent is from 20,000 to 30,000 and a viscosity at an initial mixing stage is from 5 to 7 Pa.S (5,000–7,000 cP). For instance, it is 2-Hr hardened type Devcon 2-Ton Epoxy. Usual epoxy resins mainly comprise amine and epoxy of large molecular weight and, in addition, they also contain various amine and epoxy components of small molecular weight. If the epoxy resin is used as it is for the bonding of the zirconium type fluoride glass fiber, a chemical reaction occurs between the amine and the epoxy components of small molecular weight and the zirconium type fluoride glass fiber till the epoxy becomes hardened, thereby reducing the durability of the zirconium type fluoride glass fiber against laser energy.

Further, if epoxy resin is used as the adhesive, the connection portion of the first fiber portion tends to be destroyed by the heat energy of the laser beam prior to the second fiber portion formed to the top end, so that there may be considered such a problem that expensive zirconium type fluoride glass fibers have to be replaced frequently.

In addition, infection of virus or the like has caused a problem in recent years and it has now become a common practice to use a disposable probe to be inserted into a living body but there is a problem that it is impossible to make only the top end of the probe disposable in the conventional system.

Accordingly, it has been keenly demanded for the advent of a technique capable of accurately and easily positioning a core of a first fiber having a core diameter of less than 260 μm and a core of a second fiber at a top end portion, adaptable to a disposable method of using the top end portion and for connecting the first fiber portion and the second fiber portion with excellent durability.

DESCRIPTION OF THE INVENTION

Description will now be made to a preferred embodiment of the present invention with reference to the drawings.

[First Embodiment]

Figure 1:
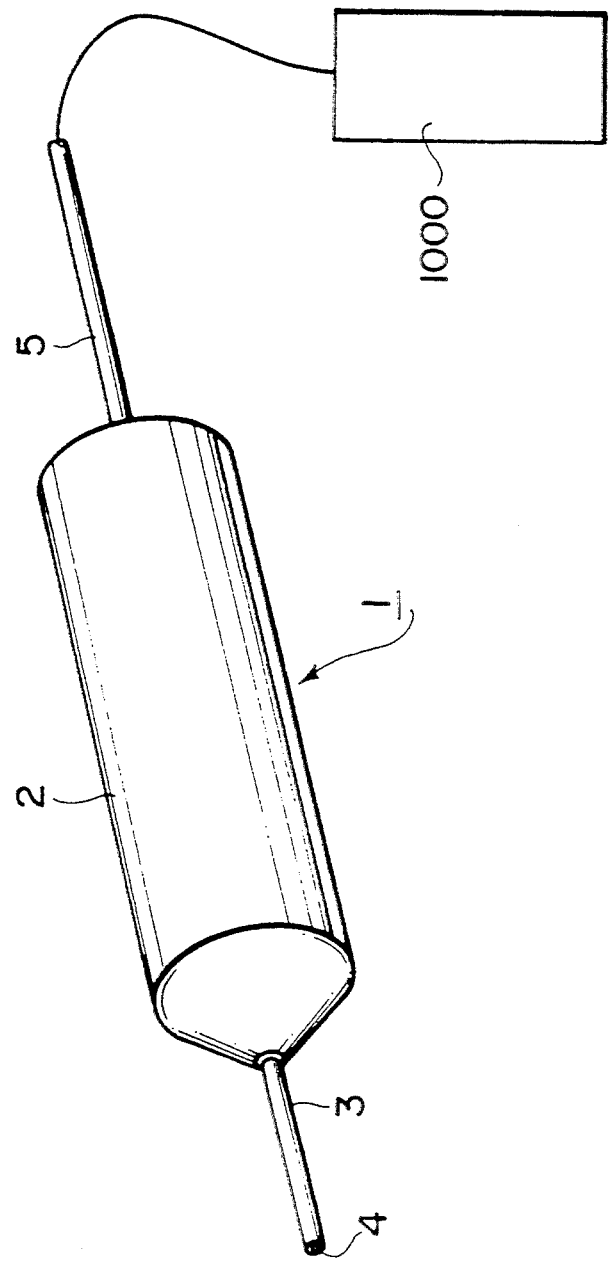
FIG. 1 is a perspective view of an intraocular operation device 1 according to the present invention.

An intraocular operation device 1 of a first embodiment comprises, as shown in FIG. 1, a hand piece 2, an intraocular probe 3, a top end fiber 4 inserted into the intraocular probe 3 and a fiber 5 for connecting the top end fiber 4 with an infrared laser light source 1000. In the intraocular operation device 1, a main body provided with the fiber 5 and a top end portion provided with the top end fiber 4 are disposed separably from each other.

The intraocular probe 3 is formed to the hand piece 2, and the top end fiber 4 is inserted inside the intraocular probe 3. The top end fiber 4 is connected by way of the fiber 5 to the infrared laser optical source 1000, so that an infrared laser beam emitted by the infrared laser light source is guided to the top end portion of the intraocular probe 3. Then, intraocular tissues can be incised by the laser beam emitted from the top end portion of the intraocular probe 3. An intraocular region corresponds to a region to be irradiated.

The infrared laser light source emits an infrared laser beam at a wavelength of about 2.9 μm. In this embodiment, an Er/YAG (erbium yttrium aluminum garnet) laser light source is adopted but other laser emitting light sources can also be used.

A more detailed description will now be made to highlight the effect of an infrared laser beam an living tissue.

The effects of laser beams on a living body depend on numerous factors, for example, wavelength, energy or power intensity, and difference of waveform such as continuous wave or pulsative wave. The effects of a laser beam can be classified into four regions, namely, the photochemical, thermal, photoablative and electromechanical regions. The thermal region is used as a laser scalpel.

The temperature of the living tissue irradiated by the laser is elevated, because of a rapid increase of molecular temperature in a case when the rotational vibration band of molecules at a low excited state by absorption of photons does not conduct spontaneous emission. Since the depth reached by the energy of the laser beam or the temperature of the tissue attained is determined by the combination of wavelength, irradiation time and irradiation area of the laser beam, control is possible including the suppression of cell activity, as well as melting, coagulation, carbonization and evaporation of proteins.

For instance, an Ar laser can coagulate a retinal choroid to 60°–70° C. under the irradiation of several tens msec, while a carbonic gas laser of continuous wave can elevate the temperature of living body tissues to higher than 100° C. and evaporate the tissues while forming a carbide layer therearound and, accordingly, it can be used for an incising operation when a hemostatic effect is desired.

Further, if a laser having a wavelength coincident with an absorption peak of water as a main constituent ingredient of the living tissues at a high peak power and at an ultra-short pulse width, the living tissues can be incised scarcely undergoing thermal damages. Then, since water has an intense absorption peak at a wavelength of about 2.9 μm and the living tissues can be incised scarcely undergoing thermal damages by using a HF laser (multi-spectra: 2.74–2.96 μm) or Er/YAG laser (wavelength of 2.936 μm) oscillating at a wavelength nearly equal with that wavelength.

Then, as the conditions capable of evaporating only the desired living tissues without giving remarkable thermal damages, such as denaturation or coagulation of protein, to tissues adjacent to the incised portion, it has been known that the exposure duration time of the infrared laser beam at a wavelength of about 2.9 μm is less than 1.7 μsec.

Accordingly, an incising operation can be conducted without pressure, by using an infrared laser beam at a wavelength of about 2.9 μm and a pulse width of less than 1.7 μsec. Particularly, the intraocular operation device 1 as in this embodiment can perform a precise operation while minimizing the exit diameter of an infrared laser emitted from the top end of the intraocular probe 3.

Figure 2:
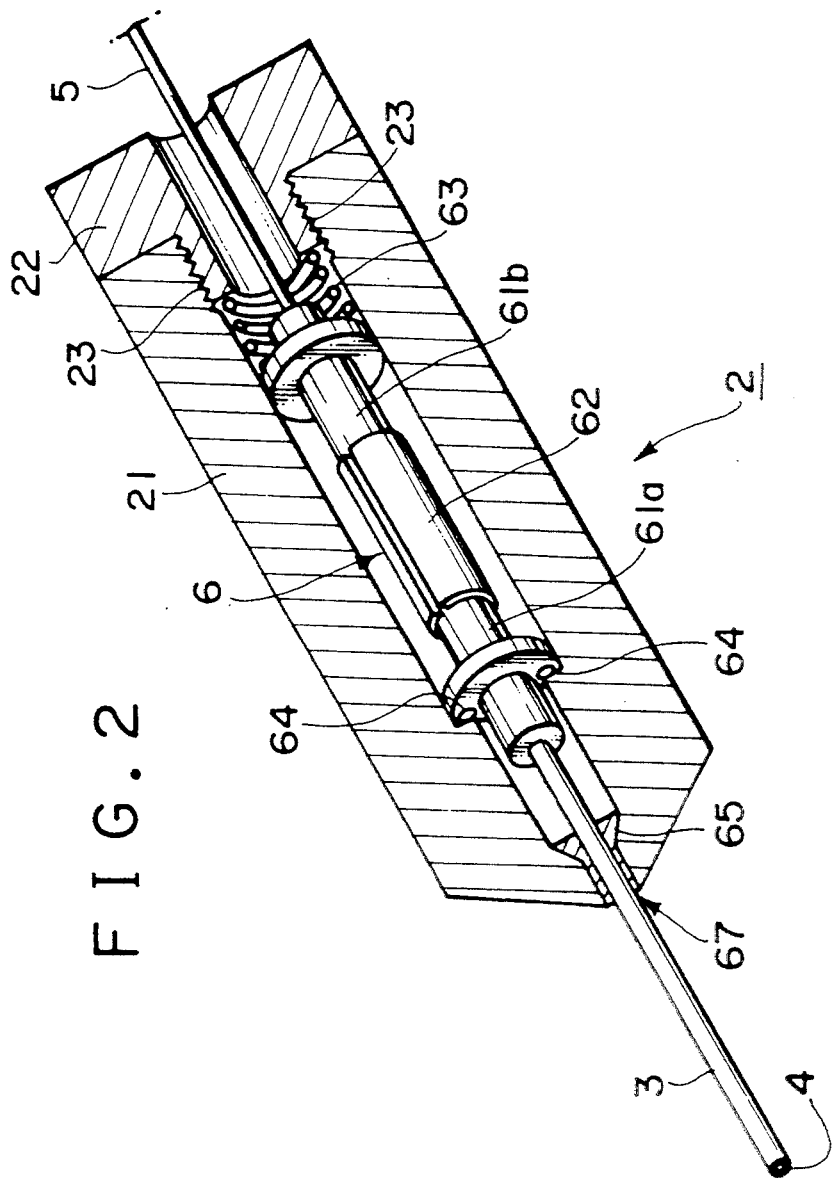
FIG. 2 is a cross sectional view of a hand piece 2 according to the present invention.

FIG. 2 is a cross sectional view of the hand piece 2, in which the intraocular probe 3 is disposed.

A top end fiber 4 is inserted through the inside of the intraocular probe 3, and the top end fiber 4 and a fiber 5 are connected by a connection means 6. The fiber 5 corresponds to a first fiber portion while the top end fiber 4 corresponds to a second fiber portion. Then, a connection surface, that is, an end face of the top end fiber 4 and a connection surface, that is, an end face of the fiber 5 are connected by way of the connection means 6.

The connection means 6 comprises ferrules 61a and 61b, a split sleeve 62 and coil springs 63.

The ferrules 61a and 61b are connectors for holding the fiber in which the ferrule 61a holds the top end fiber 4 in the intraocular probe 3, while the ferrule 61b holds the fiber 5, and the ferrules 61a and the ferrule 61b are connected by the split sleeve 62. As a result, the top end fiber 4 and the fiber 5 are connected.

Further, the hand piece 2 comprises a hand piece main body 21, and a cap member 22 to be attached to the hand piece main body 21, and the hand piece main body 21 and the cap member 22 are screw coupled by a screw means 23. Then, by inserting the coil springs 63 to the ferrule 61b from the direction of the fiber 5 and screwing the cap member 22 into the hand piece main body 21, the ferrule 61b is brought into an intimate contact with the ferrule 61a using the split sleeve 62 as a guide by way of the coil spring 63.

A packing 64 and filling adhesives 65 serve to prevent a water content in a living body from intruding through a gap 67 between the intraocular probe 3 and the hand piece main body 21 to the inside of the hand piece 2.

Figure 3:
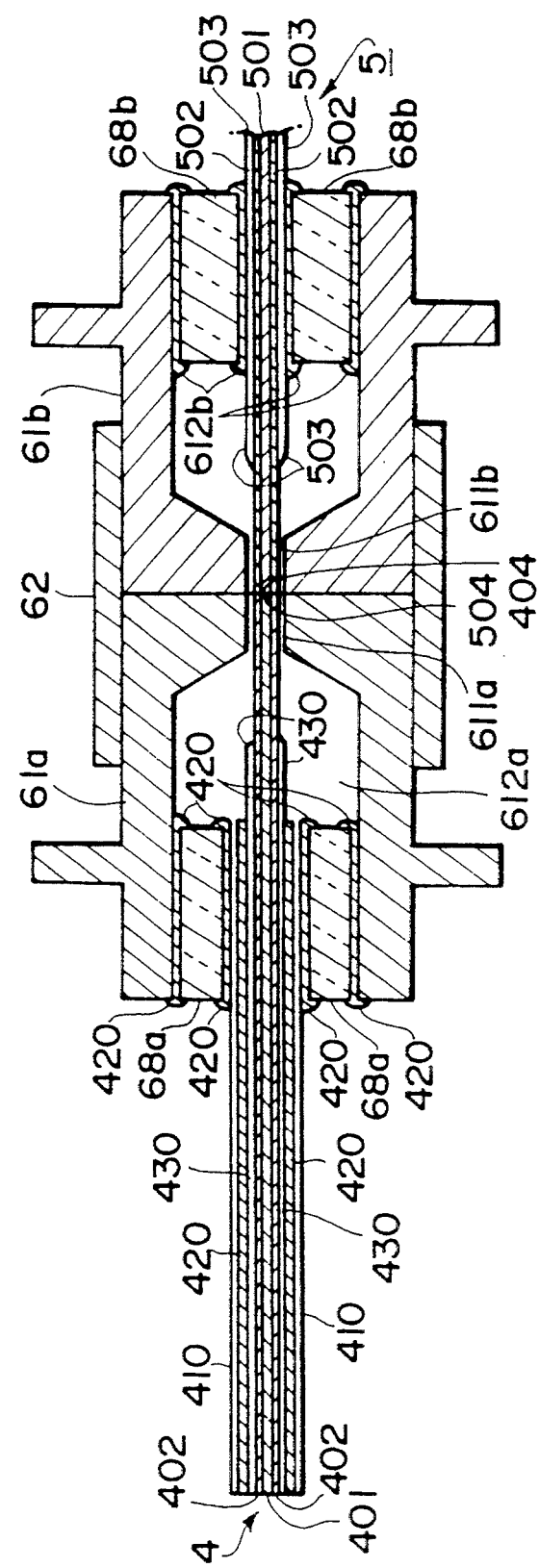
FIG. 3 is a cross sectional view showing a first embodiment of a connection means 6.

FIG. 3 is an enlarged cross sectional view for the connection portion between the top end fiber 4 and the fiber 5 connected by the connection means 6.

The ferrule 61a opens at one end and has a small aperture 611a perforated at the other end through which the top end fiber 4 passes. Further, a guide 68a is inserted into the opened end for holding the top end fiber 4.

In the same manner, the ferrule 61b opens at one end and has a small aperture 611b perforated at the other end, through which the fiber 5 passes. Further, a guide 68b is inserted into the opened end for holding the fiber 5. Then, the split sleeve 62 positions and connects the ferrule 61a and the ferrule 61b. Further, the split sleeve 62 is secured by an appropriate means such as adhesive or pins to the ferrule 61b.

The outer diameter of the ferrule 61a is usually $2.499 \pm 0.001$ mm$\phi$, the offset between the outer diameter of the ferrule 61a and the center of the small aperture 611a is usually within 0.0020 mm, and the accuracy of the hole diameter of the small aperture 611a is usually set to an aimed value $\pm 0.0010$ mm$\phi$.

The fiber 5 used in this embodiment is made of a zirconium type fluoride glass fiber, and comprising a core portion 501 of $200 \pm 5$ $\mu$m$\phi$ and a clad portion of $250 \pm 5$ $\mu$m$\phi$ and it is inserted through the guide 68b into the small aperture 611b of the ferrule 61b. The fiber 5 is secured at the inside of the ferrule by filling adhesives 612b. Then, after peeling a buffer layer 503 and polishing an end face 504, the end face 504 is inserted to the fiber 5. The buffer layer 503 is a protection layer formed for the protection of the fiber.

That is, the fiber 5 is secured to the ferrule 61b corresponding to the first terminal at a position apart from the end face 504 as the connection surface by means of filling adhesives 612b. Then, the fiber 5 having the ferrule 61b on the side in contact with the ferrule 61a corresponding to the second terminal and not coated with the filling adhesives 612b is constituted by peeling the buffer layer 503 and polishing the end face 504.

The adhesives used herein are, for example, 2-component 2-Hr hardening type Devcon 2-Ton Epoxy, which is previously applied with a dehydrating treatment before mixing by using a dehydrating agent, for example, Molecular Sieves 4A 1/16. The adhesives have the following properties the molecular weight of the epoxy as the main agent is from 200,000 to 300,000, the molecular weight of the amine as the hardening agent is from 20,000 to 30,000 and the viscosity at an initial mixing stage is from 5 to 7 Pa.S (5,000 to 7,000 cP). This results in an adhesive having a high adhesion strength, low hardening shrinkage and a complete hardening rate which is excellent. The amine and epoxy components of small molecular weight and the water content are substantially removed by the dehydrating treatment. The main agent and the hardening agent applied with the dehydrating treatment are accurately weighed to the order of 0.1 mg unit by using a chemical balance and then mixed. By using the mixture for adhesion, the complete hardening rate can be improved and the zirconium type fluoride glass fiber can be bonded to the ferrules without chemically damaging the fiber.

Further, the top end fiber 4 in this embodiment is made of a low OH quartz fiber comprising a core portion 401 of $200 \pm 5$ $\mu$m$\phi$ and a clad portion 402 of $240 \pm 5$ $\mu$m$\phi$. Then, after peeling a buffer layer 430 and polishing an end face 404, it is inserted through the guide 68a into the small aperture 611a of the ferrule 61a. The top end fiber 4 is inserted into a stainless tube 410 as far as an inside 612a of the ferrule, and the top end fiber 4 and the stainless tube 410 are secured by means of filling adhesives 420. Then, the top end fiber 4 is secured together with the stainless tube 410 by means of the filling adhesives 420 at the inside of the ferrule.

That is, the top end fiber 4 is secured to the ferrule 61a corresponding to the second terminal at a position apart from the end face 404 as the connection surface by means of the filling adhesives 420. Further, the top end fiber 4 having the ferrule 61a on the side in contact with the ferrule 61b corresponding to the first terminal and not coated with the filling adhesives 420 is constituted by peeling a buffer layer 430 and polishing the end face 404.

Since adhesive, which tends to absorb infrared energy at a wavelength of 2.9 $\mu$m thereby generating heat, are not filled to a connection portion between the fiber 5 and the top end fiber 4, this reduced the risk of thermal damage to the fiber 5.

As has been described above, the fiber 5 and the top end fiber 4 can be connected at a high accuracy by abutting them against each other after polishing each of the top ends on the side of the ferrule 61a and on the side of the ferrule 61b, and bringing the ferrule 61a and the ferrule 61b into an intimate contact with each other by the split sleeve 62.

In this embodiment, the fiber 5 may be made of a zirconium type fluoride glass fiber having a core diameter of 40 $\mu$m to 250 $\mu$m, and the low OH quartz fiber of the top end fiber 4 may have a core diameter larger than the diameter of the fiber portion. Furthermore, the end face 404 and the end face 504 correspond to the connection surface.

Figure 4:
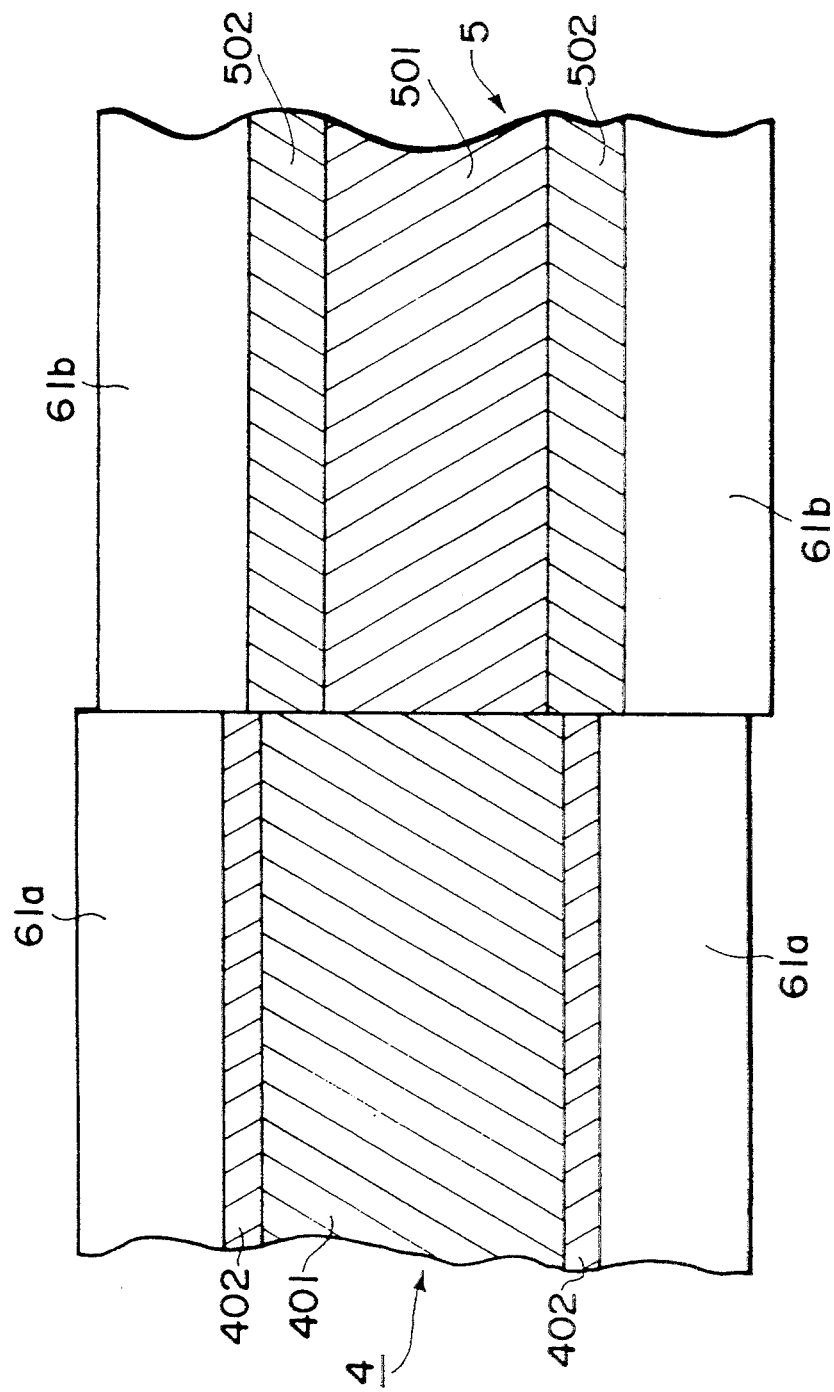
FIG. 4 is a cross sectional view showing the interface of the fiber and the top end fiber.

Using the above-described connection means 6, if all of the errors caused on the side of the ferrule 61a and the side of the ferrule 61b are added to opposite directions thereby resulting in a maximum error, the amount that the core portion 501 of the fiber 5 displaces from the core portion 401 of the top end fiber 4 as shown in FIG. 4 is extremely small. Further, even if they were displaced, since adhesives absorbing an infrared energy at a wavelength of 2.9 μm to generate heat are not filled to the connection portion between the fiber 5 and the top end fiber 4, the risk of thermal damage to the fiber 5 is greatly reduced.

Further, the top end fiber 4 is made of the low OH quartz fiber having a relatively good transmittance for an infrared laser beam at a wavelength of about 2.9 μm, and the fiber 5 made of the zirconium type fluoride glass fiber is connected at the inside of the hand piece 2. While the zirconium type fluoride glass fiber has an extremely good transmittance for the infrared laser beam at a wavelength of about 2.9 μm, it is not harmless to a human body. Accordingly, the fiber 5 has to be kept from contact with living tissues even when it is destroyed upon failure, accident or the like, and the top end fiber 4 must have a sufficient axial length. The zirconium type fluoride glass fiber 5 comprises the core portion 501 and the clad portion 502.

Using the above-described structure, a portion from an intraocular probe 3 including the top end fiber 4 can be made disposable, and the fiber 5 and the top end fiber 4 can always be connected accurately.

In this embodiment, a portion from the intraocular probe 3 to the ferrule 61a on the side of the top end fiber 4 corresponds to the top end portion, while a portion from the ferrule 61b to the fiber 5 corresponds to the main body portion. Additionally, the ferrule 61b corresponds to the first terminal while the ferrule 61a corresponds to the second terminal. When the top end portion and the main body portion are separated, the slit sleeve 62, secured to the ferrule 61b, serves to protect the top end of the fiber 5.

To minimize the effect of shock waves on a corneal endothelium when an infrared laser beam at wavelength of about 2.9 μm is irradiated pulsatively, it is desirable to minimize the energy irradiated by one shot of pulses. However, since the energy density required for evaporating living tissue by an infrared laser beam at a wavelength of about 2.9 μm is 2 J/cm², incision can not be conducted at an energy density less than that. Accordingly, it is necessary to restrict the irradiating area of the infrared laser beam as much as possible in order to evaporate the living tissue and, at the same time, minimize the effect of the shock waves.

In this embodiment, the diameter of the top end fiber 4 is about 80 μm to 250 μm. The thermal effect of the laser irradiation on an eyeball will be as follows:

The cross sectional area Ar of a sapphire rod 221a is defined as:

$$\pi*(80/2*10^{-4})^2 \leq Ar \leq \pi*(250/2*10^{-4})^2 5*10^{3}1$$
$$5 \leq Ar \leq 4.9*10^{-4} \quad (cm^2)$$

Accordingly, since the energy E applied at 2 J/cm² is 2 J/cm²*Ar, the energy required for evaporating living tissues is expressed as:

$$0.1 \text{ mJ} \leq E \leq 1.0 \text{ mJ}$$

Further, assuming the diameter of an eyeball as 24 mm, the volume of the eyeball is 7.2 cm³. Then, if a circular incision is conducted for a diameter 5 mm to a lens capsule, the incising length S is expressed as:

$$S = 5*\pi = 15.7 \text{ mm}$$

and the number of pulses required for the circular incision is expressed as:

$$(15.7/(80*10^{-3})) = 196$$

(in a case where the diameter of the top end fiber 4 is 80 μm)

$$(15.7/(250*10^{-3})) = 63$$

(in a case where the diameter of the top end fiber 4 is 250 μm).

Then, the temperature elevation of the entire eyeball in this case is expressed as:

$$((0.1*10^{-3}*4.2)cal*196)/7.2 = 0.011° \text{ C}.$$

(in a case where the diameter of the top end fiber 4 is 80 μm)

$$((1.0*10^{-3}*4.2)cal*63)/7.2 = 0.037° \text{ C}.$$

(in a case where the diameter of the top end fiber 4 is 250 μm)

Accordingly, when using the intraocular operation device 1 in this embodiment, the undesired effect of heat on the eyeball is negligible.

Although the descriptions have been made to the intraocular operation device, the present invention is also applicable to other fields requiring accurate incisions for tissue such as in the dentistry or plastic surgery.

Further, the present invention may also be applied as an effective therapeutical method for treating glaucoma.

The adhesives used in this embodiment are dehydrated with a dehydrating agent and have the following features: the epoxy as the main agent has a molecular weight of 200,000 to 300,000, the amine as the curing agent has a molecular weight of 20,000 to 30,000 and the viscosity at the initial mixing stage is from 5 to 7 Pa.S (5,000 to 7,000 cP). In addition, since the adhesives have a great adhesion strength, with less hardening shrinkage and an excellent complete hardening rate, for example, 2-component 2-Hr hardening type Devcon 2-Ton Epoxy which is accurately weighted to the order of 0.1 mg unit by using a chemical balance and mixed are used for the adhesion, the zirconium type fluoride glass fiber can be bonded with the ferrule without giving chemical damages to the fiber.

[Second Embodiment]

Figure 5:
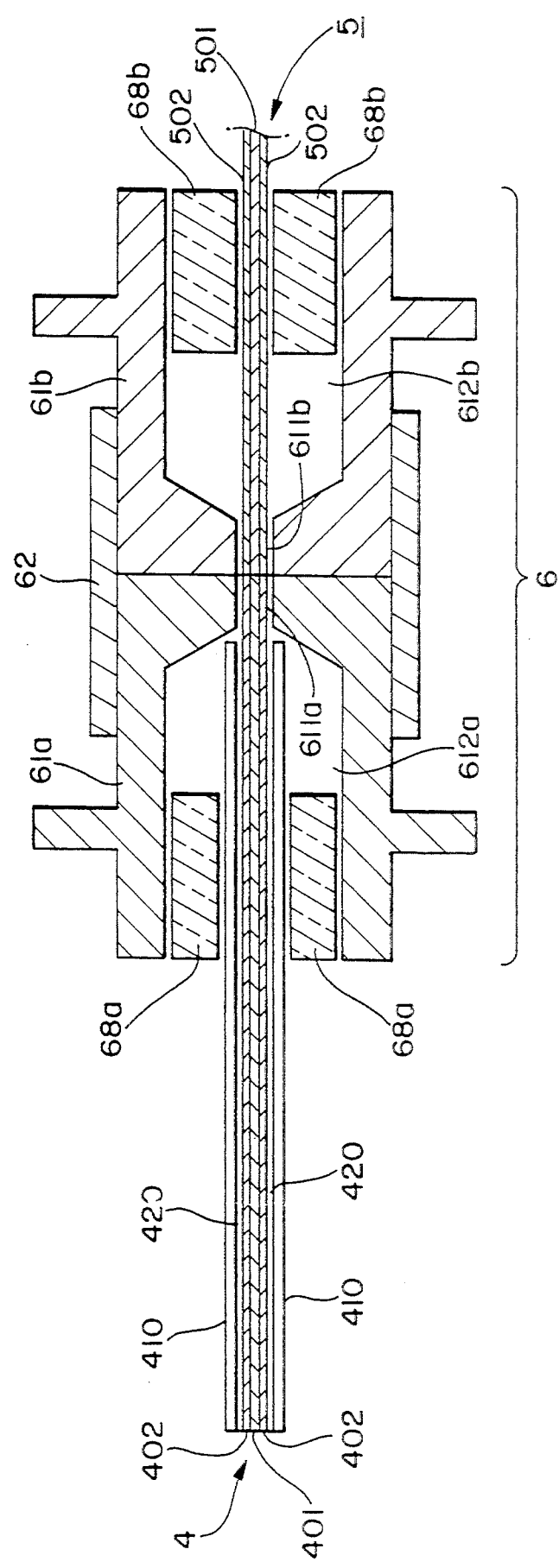
FIG. 5 is a cross sectional view for a connection means 6 in a second embodiment.

FIG. 5 showing a second embodiment is an enlarged cross sectional view for a connection portion between a top end fiber 4 and a fiber 5 connected by means of a connection means 6.

In the second embodiment, the fiber 5 is passed through a guide 68b and inserted into a small aperture 611b of a ferrule 61b. Then, after polishing a top end portion, the fiber 5 is secured together with the ferrule 61b by filling adhesives filled to an inside 612b of the ferrule.

Further, in the second embodiment, the top end fiber 4 is passed through a guide 68a and inserted into a small aperture 611a of a ferrule 61a. The top end fiber 4 is inserted in a stainless tube 410 as far as an inside 612a of the ferrule, in which the top end fiber 4 and the stainless tube 410 are secured by filling adhesives 420. Then, after polishing the top end portion, the top end fiber 4 is secured to the stainless tube 410 by filling adhesives filled to an inside 612a of the ferrule and further secured also to the ferrule 61a.

As has been described above, the fiber 5 and the top end fiber 4 can be connected at a high accuracy, after polishing each of the top end portions on the side of the ferrule 61a and on the side of the ferrule 61b, by abutting them against each other and bringing the ferrule 61a and the ferrule 61b into contact with each other by a split sleeve 62.

In the present invention having thus been constituted, a first fiber portion is adapted to guide a light from a laser light source at a wavelength corresponding to an absorption peak of water as far as the hand piece, and a second fiber portion connected at a connection surface of the first fiber portion is adapted to introduce a light from the first fiber portion to a region to be irradiated. A split sleeve connects the first terminal formed at the end of the first fiber portion and the second terminal formed at the end of the second fiber portion to provide an effect capable of facilitating alignment between the first fiber portion and the second fiber portion.

Further, even if the top end portion comprising the second fiber portion or the like were destroyed by the energy of the laser beam caused by a failure, accident or the like, it can provide an advantageous effect that the first fiber portion is not in contact with an intraocular tissue or the like as a region to be irradiated. Accordingly, this can provide an advantageous effect of enabling a safe and accurate incising operation to the eyeball tissue or the like.

The laser light source may be an infrared laser light source at a wavelength of about 2.9 $\mu$m, the first fiber portion may be made of a zirconium type fluoride glass fiber and the second fiber portion may be made of a low OH quartz fiber.

The core diameter for the first fiber portion may be from 40 $\mu$m to 260 $\mu$m and the core diameter for the second fiber portion may be made larger than the core diameter for the first fiber portion.

Further, the split sleeve is attached to the main body portion, so that the split sleeve can protect the top end of the first fiber portion. It is possible to use the top end portion in a disposable manner to prevent infection of virus or the like.

The first fiber portion is secured to the first terminal by means of adhesive at a position apart from the connection surface, and the first terminal portion in contact with the second terminal and not coated with the adhesives can also be constituted by previously peeling the fiber protecting buffer layer and polishing the end face. The second fiber portion is secured to the second terminal by the adhesives at a position apart from the connection surface, and the second terminal at a portion on the side in contact with the first terminal and not coated with the adhesives can also be constituted by previously peeling the fiber protecting buffer layer and polishing the end face. Accordingly, adhesive, which can absorb infrared energy at a wavelength of 2.9 $\mu$m to generate heat, is not filled at the connection portion between the first fiber portion and the second fiber portion, thereby reducing the risk of thermal damage to the fiber.

Further, the adhesive can be constituted with epoxy adhesives comprising polymeric compounds applied with dehydration and having an initial viscosity from 5 to 7 Pa*S (5,000 cP-7,000 cP). The epoxy adhesives have an effect of large adhesion strength, as well as less hardening shrinkage and excellent complete hardening rate.

When a region to be irradiated situates within an eye and the laser operation device is applied to an intraocular operation device, an effect most suitable as an ophthalmic operation can be attained.

What is claimed is:

1. A laser operation device comprising a hand piece, a probe which is inserted into a region to be irradiated, a first fiber portion for guiding light to the handpiece from a laser light source at a wavelength corresponding to an absorption peak of water, a second fiber portion connected with said first fiber portion at a connection surface for introducing the light from said first fiber portion to the region to be irradiated, means for enclosing said first fiber portion and said second fiber portion, a first terminal, a second terminal, adhesive for affixing said enclosing means to the first and second terminals to secure said first and second fiber portions to the first and second terminals respectively, said enclosing means protecting said first and second fiber portions from said adhesive, and a split sleeve for guiding connection of the first terminal and said second terminal, whereby alignment between said first fiber portion and said second fiber portion is facilitated.

2. The laser operation device of claim 1, wherein the laser light source is an infrared laser light source at a wavelength of about 2.9 $\mu$m.

3. The laser operation device of claim 2, wherein the first fiber portion has a core diameter of 40 $\mu$m to 260 $\mu$m and the second fiber portion has a core diameter no smaller than the core diameter of the first fiber portion.

4. The laser operation device of claim 1, wherein the hand piece is separable into a top end portion and a main body portion, the main body portion comprising the first terminal having the split sleeve at an end thereof, the top end portion comprising said second terminal, and wherein said split sleeve provides a protecting function for the end face of said first fiber portion when the top end portion and the main body portion are separated from each other.

5. The laser operation device of claim 1, wherein the first fiber portion comprising a zirconium type fluoride glass fiber and the second fiber portion comprising a low OH quartz fiber.

* * * * *